United States Patent [19]

Verkaart et al.

[11] 4,196,727
[45] Apr. 8, 1980

[54] SEE-THROUGH ANESTHESIA MASK

[75] Inventors: Wesley H. Verkaart, Lincoln Park, N.J.; Edward A. Kippel, Suffern, N.Y.

[73] Assignee: Becton, Dickinson and Company, Rutherford, N.J.

[21] Appl. No.: 907,742

[22] Filed: May 19, 1978

[51] Int. Cl.² ............................................. A61M 17/02
[52] U.S. Cl. ................................................. 128/202.23
[58] Field of Search ............... 128/205, 188, 185, 211, 128/145.5–145.8

[56] References Cited

U.S. PATENT DOCUMENTS

| | | | |
|---|---|---|---|
| 2,666,432 | 1/1954 | Stanton | 128/205 |
| 3,721,238 | 3/1973 | Wise et al. | 128/188 |
| 4,063,913 | 12/1977 | Kippel et al. | 128/188 X |
| 4,105,732 | 8/1978 | Slingluff | 128/348 X |

Primary Examiner—Henry J. Recla
Attorney, Agent, or Firm—Kane, Dalsimer, Kane, Sullivan and Kurucz

[57] ABSTRACT

The disclosure is of improved "see-through" or visibly transparent anesthesia masks providing safety by electrical grounding. The improved masks are positively grounded between patient and anesthetic delivery system and may be moved freely on the face of the patient without interruption of the ground circuit. The improvement comprises, as a ground component for contact between an anatomical portion of a patient on which the mask is fitted and the anesthesia delivery system, an electrically conductive spring, resiliently mounted in the mask interior so as to make positive contact with the patient even if the edges of the mask are momentarily raised from sealing contact with the patient's facial parts.

5 Claims, 9 Drawing Figures

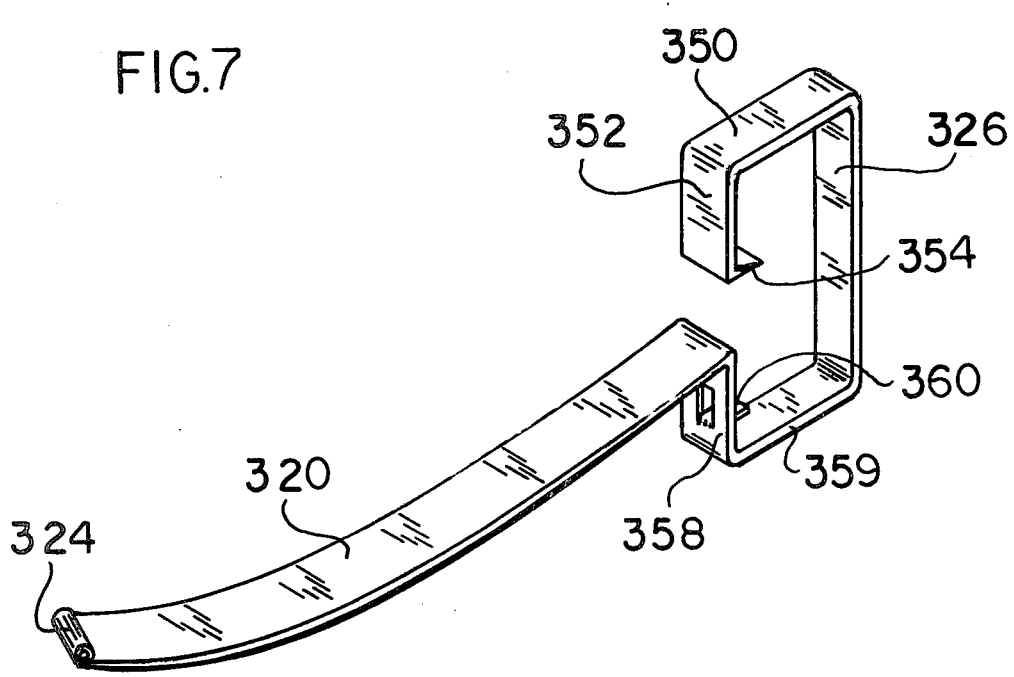
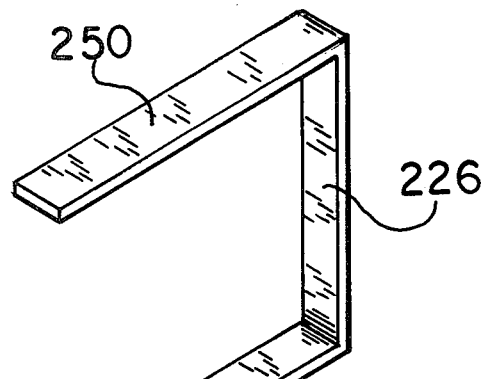
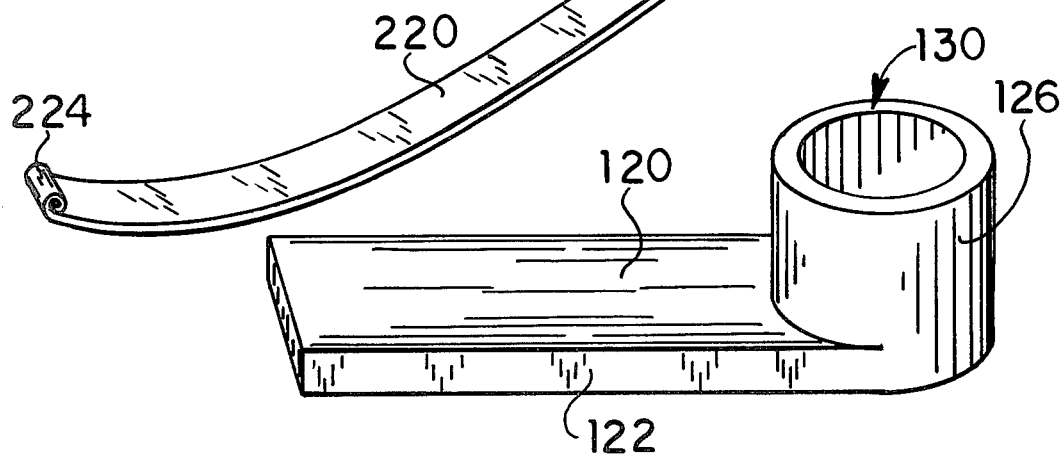

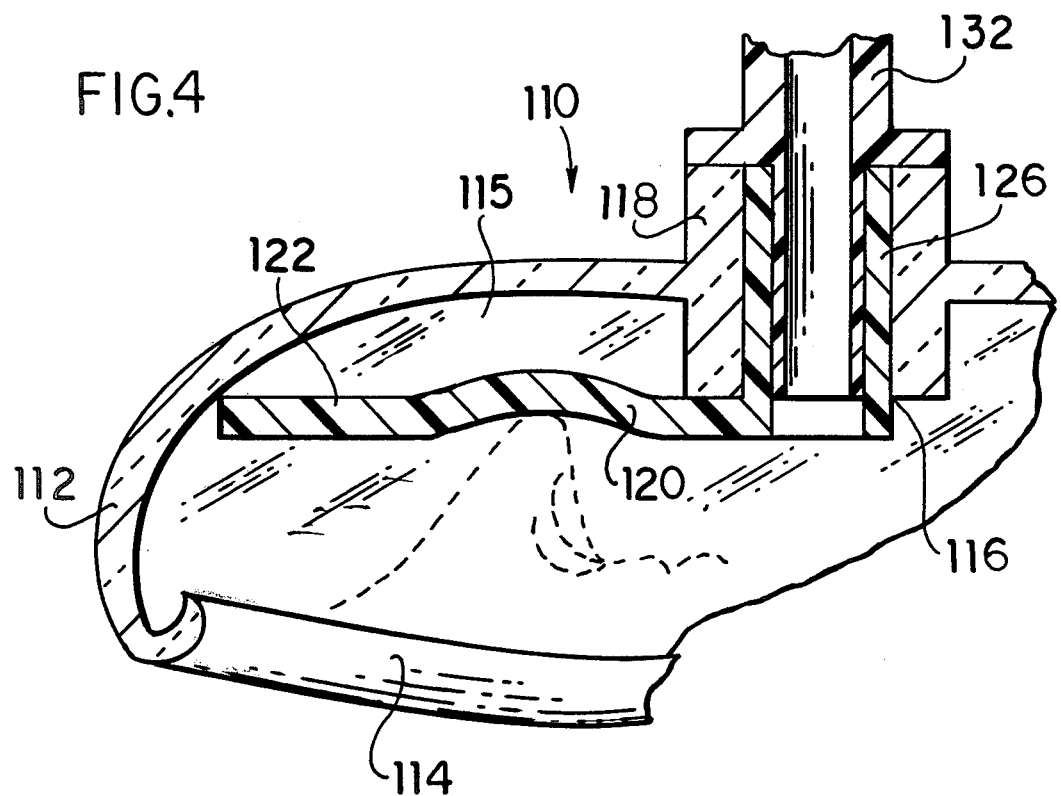

SEE-THROUGH ANESTHESIA MASK

BACKGROUND OF THE INVENTION

1. Field of the Invention

The invention relates to anesthesia apparatus and more particularly relates to electrically conductive anesthesia masks.

2. Brief Description of the Prior Art

In U.S. Pat. No. 3,721,238 there is disclosed a visually transparent anesthesia mask bearing an adhesively attached, electrically conductive, metal foil strip on its inner surface to provide a grounding strip means between patient and anesthesia delivery apparatus. Other disclosures representative of the prior art are found in U.S. Pat. Nos. 3,028,873 and 3,556,097.

The anesthesia mask of the present invention is an improvement over the prior art in that the electrical grounding means permits greater latitude in movement of the mask in use, without violating the integrity of the grounding system. Connection to the patient is more readily observable visually and impingement of the grounding means on the patient is not discomforting. Further the grounding means is replaceable when desired to assure repairs etc. The invention also permits one to readily modify a prior art mask, to incorporate the improvement of the invention.

SUMMARY OF THE INVENTION

The invention comprises, in an electrically grounded anesthesia mask having a body molded from a visually transparent, synthetic polymeric resin, said body defining an inner zone adapted to receive the mouth and nose of a patient and having a portal therethrough providing gaseous communication between the inner zone and outside of the mask, said portal being adapted to connect with an electrically grounded anesthetic delivery system, the improvement, which comprises; as an electrical ground component for connection between an anatomical portion of a patient on which the mask is fitted and the anesthesia delivery system, an electrically conductive spring, resiliently mounted on said mask in the inner zone and having one end positioned in the portal so as to make electrical contact with the grounding means associated with the anesthetic delivery system.

BRIEF DESCRIPTION OF THE DRAWINGS

FIG. 3 is an alternate embodiment grounding component shown in perspective.

FIG. 4 is a cross-sectional side elevation of an embodiment mask of the invention including the grounding component of FIG. 3, shown in use.

FIG. 5 is a view-in-prespective of still another embodiment grounding component.

FIG. 7 is a view-in-perspective of another alternate ground component for a mask of the invention.

DETAILED DESCRIPTION OF THE PREFERRED EMBODIMENTS OF THE INVENTION

Figure 2:
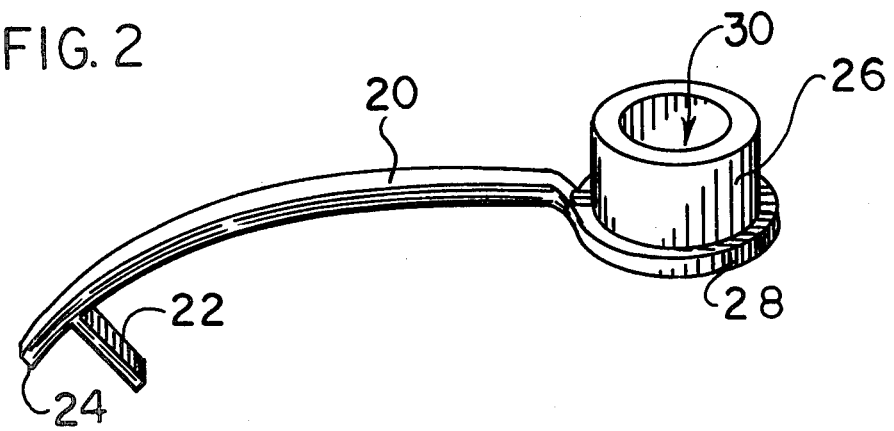
FIG. 2 is a view-in-perspective of the grounding component of the mask shown in FIG. 1.
Figure 1:
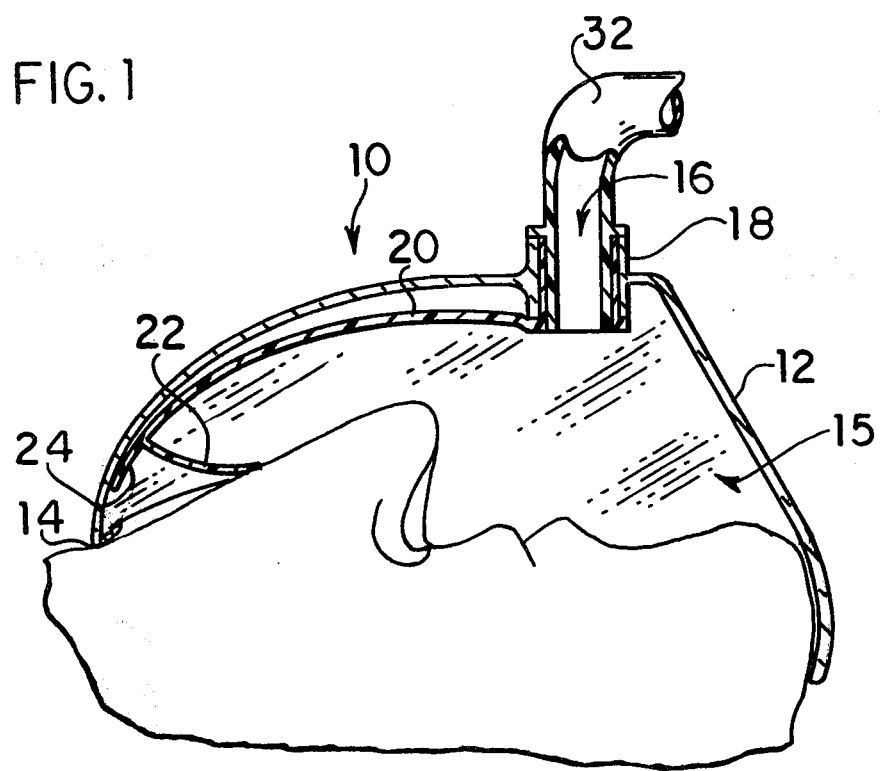
FIG. 1 is a cross-sectional side elevation of an embodiment anesthesia mask of the invention shown emplaced for use on a patient.

FIG. 1 is a cross-sectional side elevation of embodiment mask 10 of the invention, shown emplaced on a patient to be anesthesized. The mask 10 comprises a body portion 12 of molded, electrically non-conductive, visibly transparent polymeric resin such as but not limited to clear polyvinylchloride. The mask 10 has a generally semi-hemispherical shape with a lower edge 14 which is adapted by configuration to mate and seal with the face of a patient so the mouth and nose are confined within the inner zone 15 defined by the body 12 of mask 10. A portal 16 provides gaseous communication between inner zone 15 and the outside of the mask 10. Forming the peripheral boundary of portal 16 is an integrally molded (with body 12) cylinder 18 adapted to receive and mount electrically conductive grounding component 20. The electrically conductive grounding component 20 has a free tip 24 which is positioned against the inner surface of the body 12 of mask 10 at a point corresponding to the center of the mask near the bridge of the patient's nose. The opposite end of the grounding component 20 is mounted in cylinder 18 in a manner sufficient to retain it during use of the device, such as but not limited to frictional fit or solvent bonding and makes contact there with an electrically conductive anesthesia hose fitting component 32 of a conventional, electrically grounded anesthesia gas delivery system. Hose fitting 32 is secured by frictional fit in portal 16 by confinement by the walls of cylinder 26. The structure of the grounding component 20 may be seen in greater detail in FIG. 2, a view-in-perspective of the grounding component 20. The end mounted in cylinder 18 comprises an insert cylinder 26 having a passage 30 therein for receiving hose fitting 32 and a stop 28 on its lower end. The electrically conductive grounding component 20 includes a contact element 22 which, as shown in FIG. 1, presses against the patient's nose when the mask 10 is in use. Thus, the electrically conductive grounding component 20 bridges the electrical pathway gap between the electrically conductive anesthesia hose fitting 32 (attached to grounded anesthesia delivery system) and the patient. Since the grounding component 20 is centrally positioned and element 22 positively pressed against the patient by the spring action of the grounding component 20, electrical contact with the patient is maintained even if the mask 10 is lifted partially from the patient's face. This is an improvement over prior art anesthesia masks of the "see-through" type. If retained in a non-permanent manner such as by frictional fit, the grounding component 20 can also be readily removed for cleaning repair, replacement etc., when so desired by removal from its mounting in cylinder 18.

Those skilled in the art will appreciate that many modifications may be made to the configuration and style of the electrically conductive grounding component employed in the masks of the invention to bridge the otherwise occurring gap between patient and electrically grounded anesthesia delivery system. For example, referring now to FIG. 3 one may observe an alternate embodiment electrically conductive grounding component, shown in perspective. The grounding member 120 is spring-like and may be molded of a low durometer, flexible, electrically conductive material such as, but not limited to electrically conductive polyvinyl chloride. Grounding member 120 includes a resilient shank 122 portion for contacting the patient's nose within zone 115 of mask 110 (see FIG. 4). The grounding member 120 also has a cylindrical portion 126 on one end which defines a passage 130 therethrough. Referring again to FIG. 4, one may see that the resilient shank 122 is positioned within zone 115 of the embodiment mask 110 so that the patient's nose (shown in broken lines) is brought in contact therewith. The shank 122 bears resilient pressure against the patient's nose due to its contact stop at the shank 122 end with the wall 112 of mask 110. As also shown in FIG. 4, a cross-sectional side elevation of an embodiment mask 110 of the invention, the grounding element 120 is mounted in the portal 116 through wall 112 of mask 110 and receives in passage 130 by frictional engagement, an electrically conductive anesthesia hose fitting 132 in the same manner hose fitting 32 makes contact with grounding component 20 as described for the embodiment mask 10 (described above). When the side edge 114 of mask 110 is in sealing contact with the face of the patient, an electrical pathway is established between the patient's nose and the conductive anesthesia hose fitting 132. Because the shank 122 is resiliently displaced by the patient's nose, the electrical pathway may be uninterrupted even if the contact between mask edge 114 and the patient's face is broken.

Figure 6:
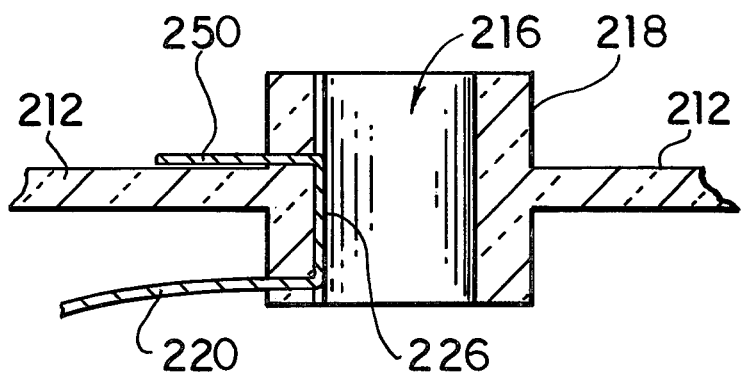
FIG. 6 is a cross-sectional side elevation of a part of the ground component of FIG. 5, shown mounted in an embodiment mask of the invention.

It is not necessary that the electrically conductive grounding component 20 or 120 include a cylinder to be mounted in the portal 16 of 116 conduit through which anesthetic gases are delivered to the interior zone 15 or 115 of the mask 10 or 110. For example, referring now to FIG. 5, a view in perspective of still another embodiment electrical grounding component of the invention, one may see that spring 220 comprises a first end 224 (which stops against the inside wall of the anesthesia mask in which it is positioned) and a second end including a vertical leg 226 and a horizontal leg 250. The electrically conductive spring 220 may be mounted in electrical contact with the hose fitting delivering anesthetic through portal 216. As shown in FIG. 6, a cross-sectional side elevation of a part of the ground component spring 220 of FIG. 5, the leg 226 is exposed on the inner surface of cylinder 218. The spring 220 is mounted in position by leg 250 secured by being molded or inserted into the body 212 (through cylinder portion 218) of an anesthesia mask. When an electrically conductive anesthesia delivery hose fitting is inserted in portal 216 it will make contact with the leg 226 of the electrically conductive grounding member 220.

FIG. 7 is a view-in-perspective of yet another embodiment of an electrical grounding component of the invention. The electrically conductive spring member 320 has a first end 324 which makes stopping contact with the interior wall of the anesthesia mask in which it is mounted. The second end of electrical grounding member 320 comprises a generally U-shaped configuration including a downward projecting leg 358, an upward or vertical leg 326, a bridging element 359, a second downward projecting leg 352 and a bridging element 350 between vertical leg 326 and the second downward projecting leg 352. The second downward projecting leg 352 includes a horizontal point 354 and the first downward projecting leg 358 includes a point 360.

Figure 8:
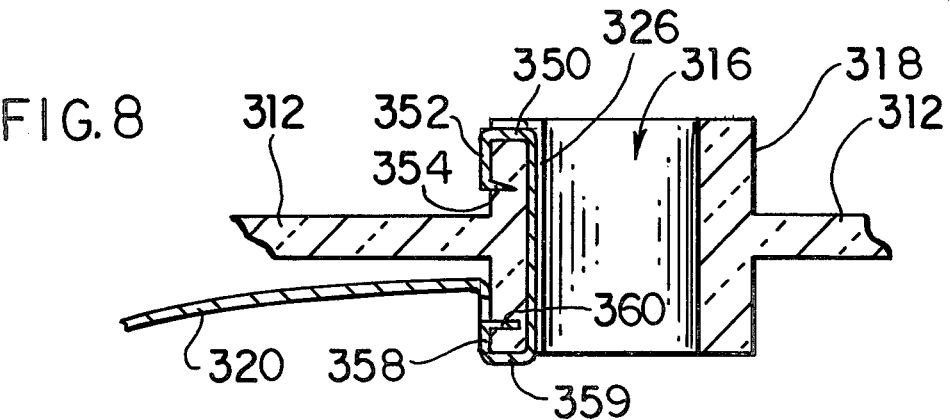
FIG. 8 is a cross-sectional, side elevation of a part of the ground component of FIG. 7, showing its mounting in a mask of the invention.

Referring now to FIG. 8, a cross-sectional side elevation of a portion of a mask within the scope of the invention one may see how the electrical grounding member 320 is mounted in association with the conduit which mates with a grounded anesthesia delivery system. The grounding member 320 may be integrally molded in place in cylinder 318 (formed in mask body 312) or fastened in place after molding so that points 360 and 354 secure the grounding member 320 to the cylinder 318 of the mask. The electrical grounding member 320 is so mounted that the vertical wall 326 is exposed in the interior of portal 316 in cylinder 318 so that when an electrically conductive anesthesia delivery hose is inserted in the portal 316 it will make contact with the vertical wall 326 of the electrical grounding component 320. In this way, elecrrical contact is provided between patient and the conventional grounding means of an anesthesia delivery system as described previously, when the mask is emplaced over a patient for use.

Figure 9:
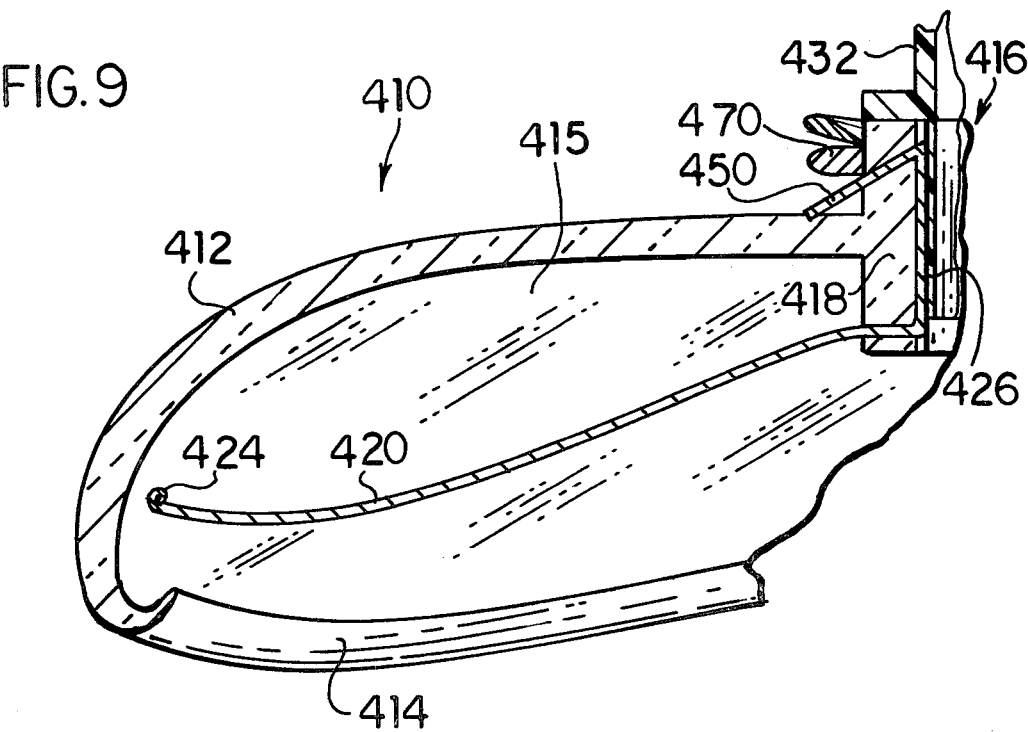
FIG. 9 is a cross-sectional side elevation of another embodiment mask of the invention.

FIG. 9 is a cross-sectional side elevation of still another embodiment electrically grounded anesthesia mask of the invention and shows mask 410 which comprises a visually transparent body portion 412 and a side edge 414 for sealing to the face of a patient and which define an interior zone 415. In interior zone 415 there is disposed an electrically conductive spring 420 having an end 424 which is stopped against the interior of wall 412 when the mask is emplaced over a patient so that the patient's nose presses upward against spring 420 (as described above for mask 10). In this manner, an electrically conductive pathway is established between the patient's nose and the electrically conductive hose 432 inserted in portal 416 of cylinder 418, which is an integral part of the body 412 of the mask 410. The spring member 420 is so mounted in the cylinder 418 that a vertical leg 426 exposed in portal 416 makes contact with the electrically conductive hose 432. Distal end 450 of spring 420 protrudes and aids to secure the spring component 420 to the mask 412 body. Electrical contact is also made to the anesthesia delivery system due to contact of the end 450 of spring 420 to the metallic clamping ring 470 which, together with an electrically conductive strap, secures the anesthetic delivery system to the patient. Those skilled in the art are familiar with grounded anesthesia delivery systems and details of such systems need not be given here; see for example the description given in U.S. Pat. No. 3,721,238.

What is claimed is:

1. In an electrically grounded anesthesia mask having a body molded from a visually transparent, synthetic polymeric resin, said body defining an inner zone adapted to receive the mouth and nose of a patient and having a portal therethrough providing gaseous communication between the inner zone and the outside of the mask, said portal being adapted to connect with an electrically grounded anesthetic delivery system, the improvement, which comprises; as an electrical ground component for connection between an anatomical portion of a patient over which the mask is fitted and the anesthesia delivery system, an electrically conductive, resilient, elongate, spring-like, grounding means mounted on said mask and extending into the inner zone and having one end secured in the portal so as to make electrical contact with the grounding means associated with the anesthetic delivery system and a second end cantilevered from said portal so as to contact said anatomical portion in the inner zone and be resiliently displaced by the anatomical portion when the mask is in place over said anatomical portion.

2. The improved mask of claim 1 wherein the grounding component is a metallic spring.

3. The improved mask of claim 1 wherein the grounding component is an elastomeric spring.

4. The improved mask of claim 1 wherein the one end is secured to the mask by integrally molding it therein.

5. The improved mask of claim 1 wherein the grounding component is so positioned that it makes resilient contact with the patient's nose.

* * * * *